US010722833B2

(12) United States Patent
Baptist et al.

(10) Patent No.: US 10,722,833 B2
(45) Date of Patent: Jul. 28, 2020

(54) PURIFICATION PROCESS

(71) Applicant: JOHNSON MATTHEY PUBLIC LIMITED COMPANY, London (GB)

(72) Inventors: Colin Baptist, North Yorkshire (GB); Claire Cahill, Cleveland (GB); Matthew John Cousins, Lancashire (GB); David Davis, County Durham (GB); Michelle Taylor Wilson, Cleveland (GB); Christopher John Young, Cleveland (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 16/128,585

(22) Filed: Sep. 12, 2018

(65) Prior Publication Data

US 2019/0009206 A1   Jan. 10, 2019

Related U.S. Application Data

(63) Continuation of application No. 14/346,880, filed as application No. PCT/GB2012/051214 on May 30, 2012, now Pat. No. 10,252,211.

(30) Foreign Application Priority Data

Sep. 29, 2011 (GB) .................................. 1116801.01

(51) Int. Cl.
| | | |
|---|---|---|
| B01D 53/02 | (2006.01) | |
| C07C 7/12 | (2006.01) | |
| B01D 15/18 | (2006.01) | |
| B01D 15/00 | (2006.01) | |
| C01B 7/07 | (2006.01) | |
| C01B 7/09 | (2006.01) | |
| B01D 15/10 | (2006.01) | |

(52) U.S. Cl.
CPC ............ *B01D 53/02* (2013.01); *B01D 15/00* (2013.01); *B01D 15/10* (2013.01); *B01D 15/1871* (2013.01); *C01B 7/0718* (2013.01); *C01B 7/093* (2013.01); *C07C 7/12* (2013.01); *B01D 2256/16* (2013.01); *B01D 2256/24* (2013.01); *B01D 2257/204* (2013.01); *B01D 2257/206* (2013.01); *B01D 2257/2045* (2013.01); *B01D 2257/2064* (2013.01); *B01D 2259/402* (2013.01); *B01D 2259/414* (2013.01); *Y02P 20/154* (2015.11)

(58) Field of Classification Search
CPC .... B01D 15/00; B01D 15/10; B01D 15/1871; B01D 2256/16; B01D 2256/24; B01D 2257/204; B01D 2257/2045; B01D 2257/206; B01D 2257/2064; B01D 2259/402; B01D 2259/414; B01D 53/02; C01B 7/0718; C01B 7/093; Y02P 20/154; C10G 25/00; C10G 25/03; C10G 25/05

See application file for complete search history.

(56) References Cited

U.S. PATENT DOCUMENTS

| | | | |
|---|---|---|---|
| 2,347,945 A | 5/1944 | Frey | |
| 3,862,900 A * | 1/1975 | Reusser | C07C 7/13 208/262.1 |
| 4,950,464 A | 8/1990 | Fujioka et al. | |
| 5,107,061 A | 4/1992 | Ou et al. | |
| 5,595,954 A | 1/1997 | Lee et al. | |
| 6,060,033 A | 5/2000 | Cheng | |
| 6,413,434 B1 | 7/2002 | Nedez | |
| 7,014,831 B2 | 3/2006 | Eicher et al. | |
| 2008/0264254 A1 | 10/2008 | Song et al. | |
| 2008/0295688 A1 | 12/2008 | Sesing et al. | |
| 2011/0005391 A1* | 1/2011 | Cho | B01D 53/047 95/97 |
| 2011/0040136 A1 | 2/2011 | Cosyns et al. | |

FOREIGN PATENT DOCUMENTS

| | | |
|---|---|---|
| EP | 1053053 A1 | 11/2000 |
| JP | 02056242 | 2/1990 |
| JP | 2592115 A | 5/1990 |
| JP | 647233 | 2/1994 |
| JP | 06-24624 B2 | 4/1994 |
| JP | 3005307 U | 12/1994 |
| JP | H07506048 A | 7/1995 |
| JP | 09-225296 A | 9/1997 |
| JP | 09-225297 A | 9/1997 |
| JP | 2001-1113124 A | 4/2001 |
| JP | 2001-302562 A | 10/2001 |

(Continued)

OTHER PUBLICATIONS

Japanese Office Action dated Apr. 12, 2016 for corresponding Japanese Application No. 2014-532463.

(Continued)

*Primary Examiner* — Derek N Mueller

(74) *Attorney, Agent, or Firm* — BakerHostetler

(57) ABSTRACT

A process is described for removing halogen compounds, particularly chlorine compounds, from a process fluid, comprising the steps of (i) passing a process fluid containing hydrogen halide over a first sorbent to remove hydrogen halide and generate a hydrogen halide depleted process fluid and then, (ii) passing the hydrogen halide depleted process fluid over a second different sorbent to remove organic halide compounds therefrom. A purification system suitable for removing hydrogen halide and organic halide compounds from process fluids is also described.

20 Claims, No Drawings

(56) References Cited

FOREIGN PATENT DOCUMENTS

| | | |
|---|---|---|
| JP | 2002-502694 A | 1/2002 |
| JP | 2002502685 A | 1/2002 |
| JP | 2003-183183 A | 7/2003 |
| JP | 2003522090 A | 7/2003 |
| JP | 2004-313876 A | 11/2004 |
| JP | 2006193563 A | 7/2006 |
| JP | 20081854512 | 8/2008 |
| WO | WO 93/22049 A1 | 11/1993 |
| WO | WO 99/39819 A1 | 8/1999 |
| WO | WO 2009126607 A2 | 10/2009 |

OTHER PUBLICATIONS

GB1116801.0, Search Report Under Section 17(5) dated Jan. 30, 2012.
PCT/GB2012/051214, International Search Report dated Oct. 8, 2012.

\* cited by examiner

PURIFICATION PROCESS

This application is a continuation of U.S. patent application Ser. No. 14/346,880, filed Jun. 17, 2014, which is the national stage of International Patent Application No. PCT/GB2012/051214, filed May 30, 2012, which claims priority from Great Britain Patent Application No. 1116801.01, filed Sep. 29, 2011, the disclosures of each of which are incorporated herein by reference in their entireties for any and all purposes.

This invention relates to purification processes and in particular to the removal of halogen compounds, particularly chlorine compounds, from gaseous or liquid process fluids.

Halogen compounds such as hydrogen chloride and organic chloride compounds may be present as contaminants in various process fluids, but are a particular problem in processing hydrogen- and hydrocarbon-containing gases and liquids, where they can cause corrosive damage to equipment and poison catalysts used in hydrocarbon processing. Typically it is desired to have a process fluid containing less than about 2 ppm, and preferably less than about 0.1 ppm, by volume of such contaminants.

WO 99/39819 (A1) describes shaped absorbent units suitable for use as chloride absorbents comprising a calcined intimate mixture of an alkali or alkaline earth, zinc and aluminium components having an alkali or alkaline earth metal to zinc atomic ratio in the range 0.5× to 2.5× and an alkali or alkaline earth metal to aluminium atomic ratio in the range 0.5× to 1.5×, where x is the valency of the alkali or alkaline earth metal, and containing from 5 to 20% by weight of a binder. Preferred compositions are made from sodium carbonate or bicarbonate, basic zinc carbonate or zinc oxide and alumina or hydrated alumina. Such materials have some capacity for organic chloride compounds in addition to their excellent hydrogen chloride sorption capacity, but processes offering improved organic chloride removal are highly desirable.

US2011/0040136 describes a process for purification by elimination of chlorine in the form of hydrogen chloride and organochlorine compounds by contacting in the presence of hydrogen of at least a part of the effluent from a reforming, aromatics production, dehydrogenation, isomerisation or hydrogenation zone, said part of the effluent comprising olefins, hydrogen chloride and organochlorine compounds, on an elimination zone comprising a chain arrangement of two masses, the first mass being a mass comprising at least one metal from group VIII deposited on a mineral carrier and the second mass being a hydrogen chloride adsorbent. In this process the Group VIII catalyst (Pt or Pd) catalyses the hydrogenation of the organochlorine compounds, which are then captured on the hydrogen chloride adsorbent.

The present invention offers an alternative process without expensive Pt or Pd hydrogenation catalysts in which a hydrogen halide sorbent is placed before an organic halide sorbent such that the organic halide sorbent is not saturated by hydrogen halide. In this way the combined removal of organic halide, which we have found may be formed on the surface of certain hydrogen halide sorbents, is improved.

Accordingly the invention provides a process for removing halogen compounds from a process fluid, comprising the steps of (i) passing a process fluid containing hydrogen halide over a first sorbent to remove hydrogen halide and generate a hydrogen halide depleted process fluid and then, (ii) passing the hydrogen halide depleted process fluid over a second sorbent to remove organic halide compounds therefrom.

The invention further provides a purification system suitable for removing halogen compounds from process fluids from process fluids comprising a first sorbent and, downstream of said first sorbent a second sorbent wherein the first sorbent removes hydrogen halide from said process fluid to generate a hydrogen halide depleted process fluid and the second sorbent removes the organic halide compounds from the hydrogen halide depleted process fluid.

By "sorbent" we hereby include adsorbent and absorbent.

The process fluid may be a hydrogen gas stream comprising preferably ≥50% vol hydrogen, more preferably ≥80% vol hydrogen, most preferably ≥90% vol hydrogen. The process fluid may be a synthesis gas stream comprising hydrogen, carbon monoxide and carbon dioxide. In some cases, the process fluid may be a gas stream comprising a hydrocarbon such as a natural gas or a refinery off-gas, containing, for example, one or more hydrocarbons such as methane, ethane, propanes, or butanes and especially one or more alkenes such as ethane, propene and butenes. Alkynes may also be present. The hydrocarbon content may be in the range 0.1-100% vol, but is preferably in the range 0.5-20% vol.

Alternatively the process fluid may be a liquid hydrocarbon stream. Such streams include liquid natural gas, natural gas liquids, condensates, LPG, kerosene, cracked naphtha and diesel fuels.

The halogen compounds are typically bromine compounds and/or chlorine compounds but more commonly are chlorine compounds. Thus by "organic halide compounds" we include in particular haloalkanes such as chloromethanes, chloroethanes, chloropropanes and chlorobutanes, as well as other longer chain chloroalkanes.

The amount of halogen compounds may vary depending upon the process fluid but the present process is particularly effective where the hydrogen halide content of the process fluid fed to the first sorbent is in the range 0.1-20 ppm.

The first sorbent may be a conventional hydrogen halide sorbent material including for example sorbents comprising carbon, alumina, alkalised metal oxides such as alkalised alumina, alkalised silica and alkalised aluminosilicate.

Preferably the first sorbent comprises an alkalised alumina, for example as described in EP1053053, and more preferably comprises an alkalised zinc-alumina composition as described in the aforesaid WO 99/39819 (A1). Hence the first sorbent preferably comprises shaped units formed from a calcined intimate mixture of:
a) an alumina component selected from alumina and/or hydrated alumina,
b) optionally a zinc component, selected from a zinc oxide, hydroxide, carbonate, bicarbonate and/or basic carbonate,
c) a basic metal component, selected from at least one compound of at least one alkali or alkaline earth metal, and
d) 5 to 20% by weight of a binder.

Preferably the first sorbent comprises a zinc component with a basic metal to zinc atomic ratio in the range 0.5× to 2.5× and a basic metal to aluminium atomic ratio in the range 0.5× to 1.5× where x is the valency of the basic metal.

Preferably the first sorbent has a basic metal content such that, after ignition of a sample of the units at 900° C., the sample has a basic metal oxide content of at least 10%, particularly at least 15%, and more particularly at least 20%, by weight. Basic metal compounds that may be employed include compounds of lithium, sodium, potassium, beryllium, magnesium, calcium, strontium and barium. Preferred compounds are compounds of sodium or calcium, particularly sodium. Particularly preferred alkali or alkaline earth compounds are carbonates and/or bicarbonates. Where an alkali metal compound is used "x"=1.

The zinc component is preferably zinc oxide, zinc carbonate or, particularly, basic zinc carbonate. The basic metal and zinc components may be present at least partially as a mixed salt, such as sodium zinc carbonate and/or basic sodium zinc carbonate.

The binder may be a suitable hydraulic cement, such as a calcium aluminate cement. Alternatively, and preferably, the binder comprises a clay, for example an acicular clay such as attapulgite or sepiolite clay.

Preferably the first sorbent is made from a mixture of hydrated alumina, sodium bicarbonate, zinc oxide or basic zinc carbonate, and a clay binder in which the alkali metal to zinc atomic ratio is above 0.8. It is especially preferred that the alkali metal to zinc atomic ratio is in the range from about 0.8 to 2.2.

The first sorbent may be made by pelleting, granulating or extruding a mixture of alumina or a hydrated alumina such as alumina trihydrate, basic metal component, optionally the zinc component, and the binder in the requisite proportions, and calcining the resultant mixture. By the term "granulating" we mean mixing the powdered ingredients, including the binder, with a little wetting agent such as water, in an amount that is insufficient to form a slurry, and forming the resultant mixture into aggregates, generally of approximate spherical configuration. Such granulation techniques are well known in the art. As an alternative to granulation, the composition may be formed into extrudates, for example using a pellet mill, for example of the type used for pelleting animal feedstuffs, wherein the mixture to be pelleted is charged to a rotating perforate cylinder through the perforations of which the mixture is forced by a bar or roller within the cylinder. The resulting extruded mixture is cut from the surface of the rotating cylinder by a doctor knife positioned to give pellets of the desired length. In order to make shaped units of adequate strength it is desirable to employ the ingredients in a finely divided form. Typically the ingredients have an average particle size in the range 1-20 μm, preferably in the range 50-10 μm. It is preferred to employ alumina trihydrate, rather than alumina, since granulation or extrusion of alumina-containing compositions tends to present processing difficulties. Where hydrated alumina is used as the alumina component, the calcination results in a substantial increase in the surface area of the absorbents. For these reasons the calcination is preferably effected at temperatures in the range 200-450° C., particularly above 240° C., and most preferably above 300° C. Preferably the calcination temperature is below 500° C. to minimise reaction of the basic metal compound and the alumina.

The first sorbent preferably has a BET surface area of at least 10 $m^2/g$, particularly above 50 $m^2/g$, and most preferably above 90 $m^2/g$.

Such materials are very effective hydrogen halide sorbents, but alumina-containing sorbents may contain acidic alumina sites that under some conditions are able to generate organic halide compounds in process fluids containing hydrogen halide and hydrocarbons such as alkenes. We have found that the alkalised zinc-alumina compositions are superior to alkalised alumina sorbents in that they produce lower levels of organic halide.

The second sorbent is different from the first sorbent and may comprise any organic halide removal material including for example alumina, carbon, zeolite, a transition metal oxide such as iron oxide and nickel oxide, and supported sorbent materials such as supported sulphonic acid, supported transition metal oxides, as well as supported barium oxide, and supported lead oxide. Preferred second sorbents comprise one or more of an alumina such as a transition alumina or a hydrated alumina, a zeolite such as zeolite Y or zeolite 13X, or a transition metal oxide selected from iron oxide, manganese oxide, copper oxide and nickel oxide.

The second sorbent may be made by pelleting, granulating or extruding a sorbent powder. Supported sorbent materials may be prepared by impregnating a granulated or extruded product with a suitable solution of a coating compound, drying and calcining the sorbent to convert the coating compound to the corresponding metal oxide. The coating compound may be an alkali coating compound, a transition metal coating compound, a lead coating compound or a barium coating compound. Suitable alkali coating compounds include sodium hydroxide, potassium hydroxide and sodium acetate. Suitable transition metal coating compounds include the metal acetates and nitrates, for example iron nitrate. Suitable lead or barium coating compounds include the nitrates. The solutions may be applied using known impregnation techniques. The level of coated metal oxide on the extruded or granulated support is preferably in the range 5-45% by weight.

In a particularly preferred embodiment, the second sorbent converts at least a portion of the organic halide present in the process fluid fed to it into hydrogen halide. The hydrogen halide may be captured on the second sorbent, and if desired, a third sorbent may be provided downstream to capture any hydrogen halide not trapped on the second sorbent.

In a particularly preferred embodiment, the second sorbent comprises a mixed transition alumina, in the form of granulated or extruded shaped unit comprising 1-10% wt binder. The transition alumina may be derived from gibbsite, boehmite or bayerite. The transition alumina may be a gamma-alumina, delta-alumina, theta-alumina, eta-alumina or chi-alumina, or a mixture of these phases. These materials may be formed by calcination of aluminium hydroxides and generally have a BET surface area in the range 50 to 400 $m^2/g$. Where the catalyst precursor is prepared using a gamma alumina, it is possible by the calcination and reduction procedure to convert at least a portion of this to delta alumina. A suitable alumina from which the shaped unit may be prepared may have a volume-median diameter D[v,0.5] in the range 1 to 500 μm.

Unlike the aforesaid US2011/0040136, neither the first or second sorbent need contain a Group VIII metal hydrogenating catalyst, in particular, neither need contain Pt or Pd and preferably the sorbents are essentially free of Pt or Pd.

The first and second sorbents preferably have an average particle size in the range 1-10 mm, and preferably 1-5 mm, in order to obtain the optimum balance of surface area versus pressure drop.

A preferred purification system comprises a first sorbent comprising an alkalised alumina or alkalised zinc alumina sorbent in the form of granules according to the aforesaid WO 99/39819 and the second sorbent a transition alumina granule or extrudate, a zeolite granule or extrudate, or a coated transition alumina extrudate, wherein the coating is selected from iron oxide, manganese oxide, copper oxide, nickel oxide, or sodium oxide or potassium oxide.

According to one embodiment of the process, a process fluid containing hydrogen halide and optionally one or more organic halide compounds is passed through a fixed bed of a particulate first sorbent disposed in a vessel, producing a hydrogen halide depleted process fluid preferably containing essentially no hydrogen halide. If the first sorbent comprises acidic sites the hydrogen-halide-depleted process fluid may contain organic halide compounds generated by reaction of hydrogen halide on the surface of the first sorbent. The hydrogen halide depleted process fluid recovered from the first sorbent is then passed through a second sorbent bed, which may be in the same vessel or a different vessel, that adsorbs the organic halide compounds and/or converts the organic halide compounds into hydrogen halide and captures them.

If the organic halide compounds are adsorbed, then no further treatment is required. However if the organic halide compounds are converted into hydrogen halide on the second sorbent, in order to reduce the release of halogen compounds to very low levels, the process stream may require further treatment with a third sorbent. Thus the second exit stream from the second sorbent may be passed over a third bed of sorbent for removing hydrogen halide to produce a process stream essentially free of halogen compounds. The third bed of sorbent may be in the same vessel as the first and/or second sorbent beds or in a downstream vessel. The third sorbent may be a conventional hydrogen halide sorbent material including for example sorbents comprising carbon, alumina, alkalised metal oxides such as alkalised alumina, alkalised silica and alkalised aluminosilicate. Preferably the third sorbent, where used, is the same as the first sorbent.

The purification system may be used at temperatures in the range 0 to 300° C., preferably 0-200° C. more preferably 10-100° C. and at pressures in the range 1 to 100 bar abs, preferably 1 to 40 bar abs.

The purification system is preferably used on dry process fluids, but may, in some cases, be used to treat process fluid streams containing small quantities of water, e.g. hydrocarbon streams with <0.2% water, preferably <0.1% water.

The invention will now be further described by reference to the following examples.

EXAMPLE 1: PREPARATION OF SORBENTS a) Sorbents Used as Received.

Sorbent (1) is PURASPEC™ 2250, a hydrogen chloride sorbent material comprising alkalised zinc and alumina as described in WO 99/39819 A1. It is commercially available from Johnson Matthey Catalysts.

Sorbent (2) is a mixed transitional phase alumina in the form of spheres (2.00-4.75 mm).

Sorbent (3) is an activated carbon product, RX3 extra (2×6 mm extrudates), supplied by Norit.

Sorbent (4) is a zeolite Y product, CBV500 (1.6 mm extrudates), supplied by Zeolyst.

Sorbent (5) is a zeolite molecular sieve product, 13X (1.6 mm extrudates), supplied by BDH.

b) Sorbents Prepared by Treatment.

Sorbent (6). Sorbent (2) was charged to a basket and soaked in caustic soda solution (60 g NaOH/100 ml water) for a period of 45 minutes. The basket was drained, and the saturated material calcined under air for two hours at 350° C. The resultant material comprised ca. 10 wt. % $Na_2O$ on alumina.

Sorbent (7). 123.8 g Sorbent (2) was charged to a basket and soaked in an aqueous potassium hydroxide solution (2.1 g KOH/199.4 g water) for a period of 45 minutes. The basket was drained, and the saturated material calcined under air for two hours at 350° C.

Sorbent (8) was prepared by impregnation of sorbent (2) with an aqueous iron nitrate solution. 60 ml of sorbent (2) was dried at 110° C. for 1 hr. This material was impregnated with a solution of 5.4 g of iron (III) nitrate nonahydrate dissolved in 20 ml of deionised water. The sample was then dried at 150° C. for 1 hr.

EXAMPLE 2: ORGANOCHLORIDE FORMATION OVER SORBENTS

A series of tests was conducted to assess the level of organochloride produced as a by-product of hydrogen chloride removal in the presence of unsaturated hydrocarbons. Experiments were conducted using a stainless steel gas phase reactor and a sorbent volume of 500 $cm^3$. A bed of 150 $cm^3$ of alpha alumina chips was positioned below and above the bed of sorbent material for each test run. The identity of the sorbent was varied in different test runs (as given in Table 1) to assess the relative level of organochloride that was produced for each material. The reactor was operated at a pressure of 20 barg, temperature of 35° C. and gas contact time with the catalyst of 47.9 seconds. The feed gas consisted of hydrogen, with the addition of 50 ppm hydrogen chloride and 200 ppm isobutene. Hydrogen chloride concentration at the inlet and exit of the reactor was measured using hydrogen chloride gas detection tubes. Concentrations of organochloride (tertiary butyl chloride) at the reactor exit were determined by gas chromatography. The concentration of tertiary butyl chloride in the exit stream at the end of the test run for each of the sorbents is shown in Table 1.

TABLE 1

| Sorbent | Time online (days) | Tertiary butyl chloride in exit stream at end of run (ppm) | Hydrogen chloride in exit stream at end of run (ppm) |
| --- | --- | --- | --- |
| (1). alkalised zinc-alumina | 56 | 7 | <2 |
| (6). $Na_2O$/ alumina | 57 | 49 | <2 |

These results show that, while effective for hydrogen chloride removal, the alkalised alumina-containing sorbent released significant amounts of the organic chloride compound as a by-product of hydrogen chloride removal. The alkalised zinc-alumina sorbent produced significantly less organochloride.

EXAMPLE 3: ORGANOCHLORIDE REMOVAL FROM A GAS STREAM

A series of tests was conducted to see the effectiveness of different sorbents for the removal of organochloride from a gas stream. In this case tertiary butyl chloride was used as the organochloride.

Work was conducted in a glass reactor using a sorbent volume of 60 $cm^3$. The feed gas for the reactor was 100 ppm tertiary butyl chloride in a hydrogen carrier. The feed gas was passed over the sorbent at a flow rate of 45 l $hr^{-1}$ at ambient temperature (about 20° C.) and atmospheric pressure. Samples were taken by syringe from the inlet and exit of the reactor, and levels of tertiary butyl chloride measured by gas chromatography. Each individual test was terminated when the exit tertiary butyl chloride level exceeded 5 ppm by volume. The time taken to achieve this breakthrough of 5 ppm tertiary butyl chloride is given for each sorbent in Table 2.

TABLE 2

| Sorbent | Time for 5 ppm tertiary butyl chloride to breakthrough sorbent bed (minutes) |
|---|---|
| (2) alumina | 24485 |
| (3) carbon | 11530 |
| (4) zeolite Y | 32055 |
| (5) zeolite 13X | 58105 |

In comparison, Sorbent (1) had a breakthrough time of 8695 minutes. Thus alumina sorbent (2) and Zeolite sorbents (4) and (5) are particularly effective as organochloride sorbents under these conditions.

EXAMPLE 4 ORGANOCHLORIDE REMOVAL FROM A LIQUID STREAM

A series of tests was performed to demonstrate the effectiveness of the sorbents in removing chlorine compounds at very high levels from liquid. A glass reactor was charged with a 60 cm³ bed of the sorbent. The feed (500 ppmv tertiary butyl chloride in n-heptane) was passed at ambient temperature (about 20° C.) through the reactor at 4.8 cm³/min in an upflow configuration. The test was terminated when the exit concentration of tertiary butyl chloride had reached 5 ppmv, as measured by gas chromatography. The results are given in Table 3.

TABLE 3

| Sorbent | Breakthrough time (mins) |
|---|---|
| (5) zeolite 13X | 2285 |
| (8) iron oxide/alumina | 890 |

The results demonstrate that the treated alumina or zeolite sorbents are effective in the liquid phase.

EXAMPLE 5: REMOVAL OF HYDROGEN CHLORIDE AND BY-PRODUCT ORGANOCHLORIDE USING A COMBINATION OF MATERIALS IN DIFFERENT BEDS

A series of tests was conducted to combine the effects demonstrated in Example 2 and Example 3, whereby a range of different sorbents were placed downstream of a hydrogen chloride sorbent to demonstrate the effectiveness of the second sorbent bed for the removal of by-product organochloride. The experiments were carried out using the same reactor system as described in Example 3. A hydrogen feed gas containing 1% v hydrogen chloride and 1% v propene was used. The vessel was loaded with 60 cm³ each of the first and second sorbents. The first sorbent in each case was the alkalised zinc-alumina, sorbent (1), for hydrogen chloride removal. The second sorbents are set out below in Table 4. The feed gas was fed to the vessel such that it passed through the first sorbent bed and then the second sorbent bed. The feed gas was passed over the sorbents at a rate of 45 l hr⁻¹. The reactor was operated at ambient temperature (about 20° C.) and atmospheric pressure. Gas samples were taken by syringe from the midpoint of the reactor between the first and second sorbents and the exit of the bottom bed and analysed for organochloride (by gas chromatography) and hydrogen chloride (using gas detection tubes). Breakthrough times for hydrogen chloride and organochloride were recorded. The experiment was terminated when hydrogen chloride exiting the first bed exceeded 10 ppmv, or the organochloride exciting the second bed exceeded 0.5 ppmv, whichever occurred first. The results are given in Table 4.

TABLE 4

| Second Sorbent | Time for hydrogen chloride at exit of first sorbent (sorbent A) to exceed 10 ppmv | Time for organochloride chloride exiting second sorbent to exceed 0.5 ppmv |
|---|---|---|
| (2) alumina | — | 165 mins |
| (3) carbon | 990 mins | — |
| (7) K₂O/alumina | — | 300 mins |
| (5) zeolite 13X | 1055 mins | — |

In comparison, using sorbent (1) as the second sorbent as well gave an organochloride breakthrough time of 60 mins. The choice of material in the second bed influences the ability of the purification system to prevent the passage of by-product organochloride.

What is claimed is:
1. A process for removing a halogen compound from a process fluid, comprising the steps of:
   (i) passing a process fluid containing hydrogen halide over a first sorbent comprising an alkalized alumina to remove hydrogen halide and generate a hydrogen halide depleted process fluid; and then
   (ii) passing the hydrogen halide depleted process fluid over a second sorbent comprising zeolite 13X to remove an organic halide compound.
2. The process of claim 1, wherein the process fluid is a hydrogen gas stream comprising 50% vol or greater of hydrogen.
3. The process of claim 1, wherein the process fluid is a liquid stream comprising a hydrocarbon or a gas stream comprising a hydrocarbon.
4. The process of claim 1, wherein the process fluid is a liquid stream comprising a hydrocarbon.
5. The process of claim 1, wherein the halogen compound is a bromine compound or a chlorine compound.
6. The process of claim 5, wherein the halogen compound is a chlorine compound.
7. The process of claim 1, wherein the hydrogen halide content of the process fluid fed to the first sorbent is in the range of from 0.1 to 20 ppm.
8. The process of claim 1, wherein the first sorbent comprises acidic sites that form one or more organic halide compounds.
9. The process of claim 1, wherein the process fluid from step (ii) is passed over a third sorbent to remove residual or formed hydrogen halide.
10. The process of claim 9, wherein the third sorbent is the same as the first sorbent.
11. The process of claim 1, wherein the temperature is in a range of from 0° C. to 300° C.
12. The process of claim 11, wherein the temperature is in a range of from 0° C. to 200° C.
13. The process of claim 12, wherein the temperature in a range of from 10° C. to 100° C.
14. The process of claim 1, wherein the pressure is in a range of from 1 to 100 bar abs.
15. The process of claim 14, wherein the pressure is in a range of from 1 to 40 bar abs.
16. A purification system for removing a halogen compound from a process fluid, the system comprising:

a first sorbent that removes hydrogen halide from said process fluid to generate a hydrogen halide depleted process fluid; and a second sorbent downstream of said first sorbent that removes the organic halide compound from the hydrogen halide depleted process fluid, wherein:

the first sorbent comprises pellets, granules or extrudates comprising an alkalised alumina, and the second sorbent comprises pellets, granules or extrudates comprising zeolite 13X.

17. The purification system of claim 16, wherein the first sorbent comprises acidic sites and forms one or more organic halide compounds.

18. The purification system of claim 16, further comprising a third sorbent downstream of the second sorbent, wherein the third sorbent removes hydrogen halide from the process fluid.

19. The purification system of claim 18, wherein the third sorbent is the same as the first sorbent.

20. The purification system of claim 16, wherein the first and second sorbents are in the same vessel.

\* \* \* \* \*